US00PP10023P

United States Patent [19]

Challet

[11] Patent Number: Plant 10,023

[45] Date of Patent: Sep. 9, 1997

[54] CHRYSANTHEMUM PLANT NAMED 'CHANIMBA'

[75] Inventor: Jean Pierre Challet, Nuaille, France

[73] Assignee: Selection New Plant Sarl, Le Luc, France

[21] Appl. No.: 710,105

[22] Filed: Sep. 12, 1996

[51] Int. Cl.[6] ..... A01H 5/00

[52] U.S. Cl. ..... Plt./78

[58] Field of Search ..... Plt./78

[56] References Cited

PUBLICATIONS

"Mutation studies on chrysanthemum", NBRI Newsletter, 1989, 16(1):2–3.

Datta, 1991, "Evaluation of recurrent irraliation on vegetatively propagated ornamental: Chrysanthemum", J. Nucleic Agric. Biol., 20(2):81–86.

Banerji et al., 1990, "Induction of somatic mutation in Chrysanthemum cultivar 'Anupam'," J. Nuclear Agric. Biol., 19:252–256.

Gosling, ed., 1979, "The Chrysanthemum Manual–6th edition", National Chrysanthemum Society, Essex Telegraph Press, Ltd., London, pp. 329–336.

Broertjes et al., 1978, "Application of Mutation Breeding Methods in the Improvement of Vegetatively Propagated Crops", Elsevier Sci. Pub. Co., New York, pp. 162–175.

Gupta, et al., 1978, "Mutation breeding of chrysanthemum II. Detection of gamma ray induced somatic mutations in villa", J. Nuclear Agric. Biol. 7(2):50–54.

Glazurina, et al., 1977, "Use of the method of artificial mutagenesis in the breeding of flower crops", Cytology and Genetics, vol. 11(3):42–45.

Das, et al., 1977, "Improvement of some vegetatively propagated ornamentals by gamma radiation", Indian J. Horticulture, 34(2):169–174.

Dowrick, et al., 1966 "The induction of mutations in chrysanthemum using x–and gamma radiation", Euphytica 15:204–210.

Searle, et al., 1968, "Chrysanthemums the Year Round", Blanford Press, London, pp. 27–29, 320–327.

Broertjes, 1966, "Mutation breeding of chrysanthemums", Euphytica, 15:156–162.

*Primary Examiner*—Howard J. Locker

*Attorney, Agent, or Firm*—Burns, Doane, Swecker & Mathis, L.L.P.

[57] ABSTRACT

A new and distinct Chrysanthemum cultivar named 'Chanimba' is provided. The new cultivar is a mutation that was created through gamma irradiation of the 'Chalecat' cultivar (U.S. Plant Pat. No. 9,463). Attractive very large double incurved blossoms of the pompon type are formed that are bright yellow in coloration. The incurving is particularly pronounced at the tips of the ray florets. The blossoms are long lasting and keep their form for approximately three weeks. The response time of the flowers is approximately ten weeks. Recurrent profuse flower production throughout the year is possible. The plant possesses medium to strong stems, forms attractive leaves, and commonly assumes a height of approximately 30 to 35 cm. The blossom coloration contrasts nicely with the dark green foliage. The new cultivar is particularly suited for use in the production of a decorative pot Chrysanthemum that grows well when single stem or disbudded. No growth regulator is necessary to achieve the very short to short plant height.

1 Drawing Sheet

SUMMARY OF THE INVENTION

The present invention comprises a new and distinct cultivar of Chrysanthemum, botanically known as *Dendrenthema grandiflora,* and hereinafter is referred to be the cultivar named 'Chanimba'.

The new cultivar of the present invention was created through the gamma irradiation of the 'Chalecat' cultivar (U.S. Plant Pat. No. 9,463). The parent 'Chalecat' cultivar was formed by the crossing of the 'Siky' cultivar (non-patented in the United States) and the 'Prouesse' cultivar (non-patented in the United States).

During June 1980, at Saint Paul Lez Durance, France, groups of 1,000 rooted cuttings of the 'Chalecat' cultivar having an age of two weeks were irradiated with gamma rays through the packing boxes at rates of 1.8, 2.5 and 3.0 Krads. Following irradiation the plants were shipped to Nuaille, France, and were planted in 4 liter pots, were pinched, and were grown outside until September. The plants were next grown in greenhouses, were not disbudded, and were carefully observed. It was found that most of the plants irradiated at a rate of 3.0 Krads died. Those plants that were irradiated at a rate of 2.5 Krads exhibited no growth following pinching and were discarded. Many different mutations were observed in the plants that were irradiated at a rate of 1.8 Krads. A single mutation that exhibited the characteristics of the 'Chanimba' cultivar of the present invention was discovered among these plants, as was a single mutation which exhibited the characteristics of the 'Chafeje' cultivar (copending U.S. Plant patent application Ser. No. 08/710,153). Also a single mutation that exhibits the characteristics of the 'Chahalu' cultivar (U.S. Plant Pat. No. 9,472), a single mutation that exhibits the characteristics of the 'Chatupa' cultivar (U.S. Plant Pat. No. 9,480), and a single mutation that exhibits the characteristics of the 'Chalurido' cultivar (U.S. Plant Pat. No. 9,502) were discovered among the same group of plants. It would have been impossible for a plant scientist to have predicted in advance that a new cultivar having the combination of characteristics of the presently claimed 'Chanimba' cultivar or the sister 'Chafeje' 'Chahalu', 'Chalurido' and 'Chatupa' cultivars could have been formed even if the parent 'Chalecat' cultivar would have been available for such experimentation.

It was found that the new cultivar of the present invention:

(a) exhibits attractive large double incurved pompon blossoms that are bright yellow in coloration.

(b) exhibits a flower response period of approximately ten weeks.

(c) forms attractive dark green glossy foliage.
(d) achieves a very short to short plant height, and
(e) is particularly suited for pot mum production on a recurrent basis throughout the year.

The new cultivar is intended primarily as a decorative pot Chrysanthemum for growing indoors. However, it also can be grown for cut flower production in those instances where stems of approximately 40 cm. or less are acceptable. Also, the new cultivar can be grown outdoors at temperatures above freezing.

In the absence of debudding the new cultivar commonly forms approximately 8 to 12 blossoms per stem. The new cultivar can be grown well when single stem or disbudded. An increased number of branches readily can be induced by pinching. The pinching of a cutting commonly produces approximately 3 to 4 stems per cutting. No growth regulator is required to produce the very short plant height; however, a growth regulator optionally can be utilized.

The new cultivar can be considered to be an October-flowering greenhouse variety with the natural flowering season commonly occurring in weeks 42 to 43 of the year. Attractive blossoms can be produced on a recurrent basis throughout the year with the indicated ten week response period. The blossoms are long lasting and commonly can be attractively maintained on the plant for approximately three weeks.

Asexual reproduction of the new cultivar by cuttings initially taken during 1990, as performed in Nuaille, Trementines, France, in a controlled environment has demonstrated that the characteristics of the new cultivar as herein described are firmly fixed and are retained through successive generations of asexual propagation.

'Chanimba' has not been observed under all possible environmental conditions to date. Accordingly, it is possible that the phenotype may vary somewhat with variations in the environment, such as temperature, light, day length, contact with pesticides and/or subjection to growth retardant treatments.

The 'Chanimba' cultivar of the present invention exhibits a combination of characteristics that readily distinguish it from the parent 'Chalecat' cultivar. For instance, the 'Chanimba' cultivar exhibits a bright yellow capitulum unlike the 'Chalecat' cultivar, a foliage coloration between Green Group 137A and 147A unlike the Yellow-Green Group 147A coloration of the 'Chalecat' cultivar, a stem coloration of Yellow-Green Group 144A unlike the Yellow-Green Group 146B of the 'Chalecat' cultivar, a medium to coarse leaf serration unlike the medium to fine leaf serration of the 'Chalecat' cultivar, and a cordate shape of the base of the leaf unlike the acute or slightly rounded base of the 'Chalecat' cultivar.

As indicated, other mutations of the 'Chalecat' cultivar are the 'Chafeje' cultivar, the 'Chahalu' cultivar, the 'Chatupa' cultivar, and the 'Chalurido' cultivar. Each of these additional cultivars can be readily distinguished from the 'Chanimba' cultivar with respect to a number of plants characteristics.

The 'Chafeje' cultivar exhibits a red capitulum unlike the 'Chanimba' cultivar, a foliage coloration of Green Group 139A (and sometime paler) unlike the coloration between Green Group 137A and 147A of the 'Chanimba' cultivar, and an acute and occasionally rounded leaf base unlike the cordate base of the 'Chanimba' cultivar.

The 'Chatupa' cultivar exhibits a honey gold capitulum unlike the 'Chanimba' cultivar, a foliage coloration of the Green Group 137A unlike the coloration between the Green Group 137A and 147A of the 'Chanimba' cultivar, a stem coloration between the Yellow-Green Group 144A and 144B unlike the coloration of Yellow-Green Group 144A of the 'Chanimba' cultivar, a medium leaf serration unlike the medium to coarse leaf serration of the 'Chanimba' cultivar, and a rounded tending to cordate base of the leaf unlike the cordate base of the 'Chanimba' cultivar.

The 'Chalurido' cultivar exhibits a capitulum having inner surfaces of Venetian violet and silvery lavender outer surfaces unlike the 'Chanimba' cultivar, a foliage coloration of the Yellow-Green Group 147A unlike the coloration between the Green Group 137A and 147A of the 'Chanimba' cultivar, a fine to coarse leaf serration unlike the medium to coarse leaf serration of the 'Chanimba' cultivar, and an asymmetric base of the leaf unlike the cordate base of the 'Chanimba' cultivar.

The 'Chahalu' cultivar exhibits a lemon yellow capitulum unlike the bright yellow capitulum of the 'Chanimba' cultivar. The coloration of 'Chahalu' of the outer side of most fully expanded ray florets is Yellow Group 5D, tinged with pink at the base unlike the coloration between Yellow Group 6C and Yellow Group 7C, very weakly tinged with red-purple towards the base of the 'Chanimba' cultivar. The coloration of 'Chahalu' on the inner side of majority of fully expanded ray florets is Yellow Group 5C, deepening to Yellow Group 5B at the tips unlike the coloration of Yellow Group 9B for the 'Chanimba' cultivar. The coloration of 'Chahalu' on the inner side of the inner florets is Yellow Group 5C, deepening to Yellow Group 5B at the tips unlike the Yellow Group 9A coloration for the 'Chanimba' cultivar. The foliage coloration of 'Chahalu' is between the Green Group 137A and 139A unlike the coloration between the Green Group 137A and 147A for the 'Chanimba' cultivar. The 'Chahalu' cultivar exhibits no anthocyanin coloration on the stems unlike the 'Chanimba' cultivar, a fine to coarse leaf serration unlike the medium to coarse leaf serration of the 'Chanimba' cultivar, a diverging margin of sinus between lateral leaf lobes unlike the converging margin of the 'Chanimba' cultivar, a lack of involucral bracts among florets unlike the flower head of the 'Chanimba' cultivar, the flat cross-section of short tube ray florets unlike the concave cross-section of the 'Chanimba' cultivar, a domed-flat receptacle unlike the conical-raised receptacle of the 'Chanimba' cultivar, and an acute leaf base unlike the cordate leaf base of the 'Chanimba' cultivar.

The new 'Chanimba' cultivar is being marketed under the Bright Yellow Cymbal trademark.

BRIEF DESCRIPTION OF THE PHOTOGRAPH

The accompanying photograph was prepared during March, 1996, and shows as nearly true as it is reasonably possible to make the same in a color illustration of this character, typical plants and plant parts of the new cultivar of the present invention. The plants were twelve weeks of age and were grown in Nuaille, Trementines, France, under standard greenhouse conditions which approximate those commonly utilized for the production of decorative pot mums. The plants had been disbudded except where indicated in order to encourage the formation of a single large bloom per stem.

FIG. 4 illustrates the under surface of a typical leaf from the upper part of the stem;

FIG. 14 illustrates a typical stem; and

FIG. 15 illustrates a side view of a typical inflorescence wherein no disbudding was practiced.

DETAILED DESCRIPTION

Figures 1, 2, 3, 5, 6, 7, 8, 9, 10, 11, 12, 13:
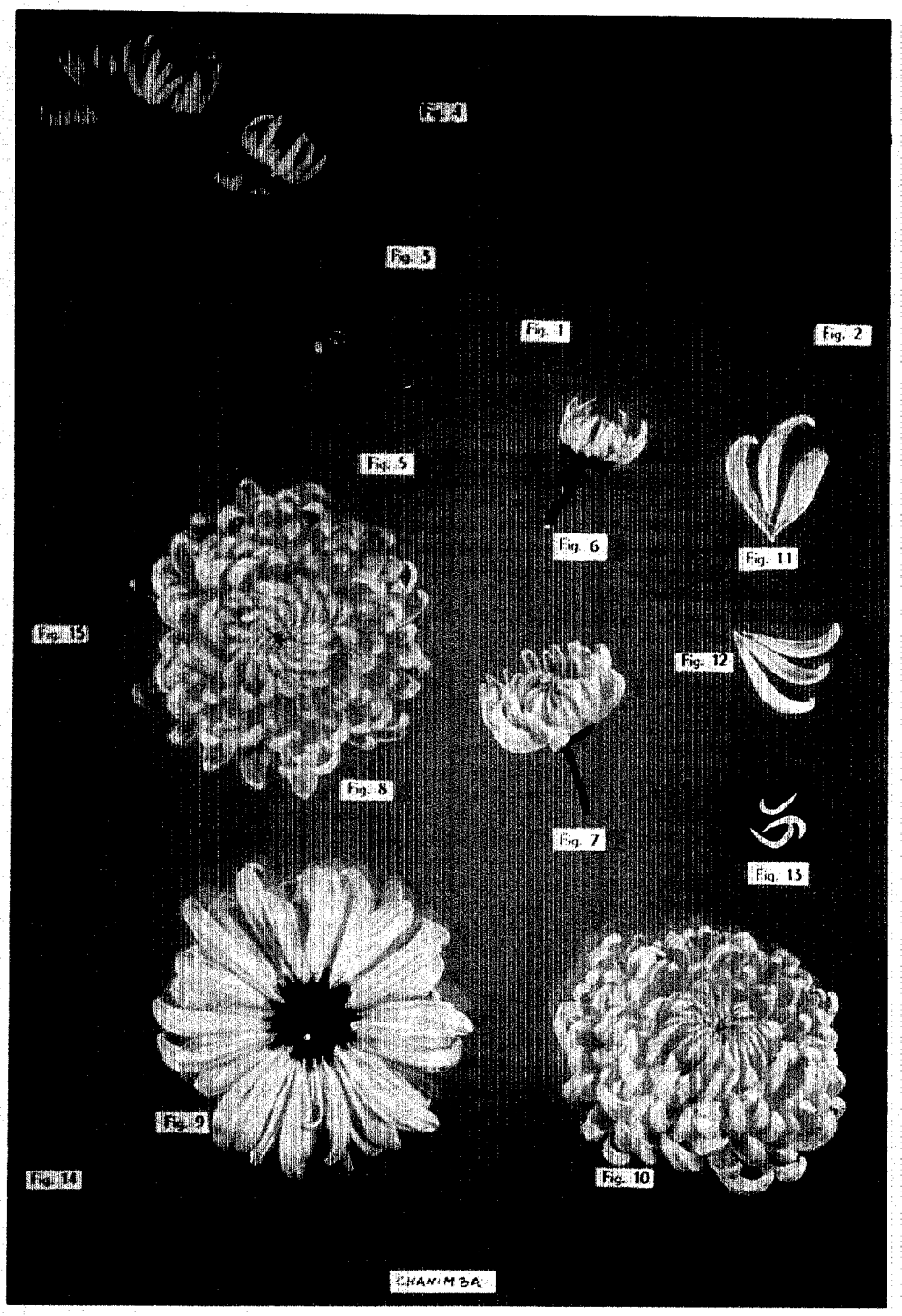
FIG. 1 illustrates the upper leaf surface of a typical leaf from the lower part of the stem.
FIG. 2 illustrates the under leaf surface of a typical leaf from the lower part of the stem.
FIG. 3 illustrates the upper surface of a typical leaf from the upper part of the stem.
FIG. 5 illustrates the side view of an unopened bud.
FIG. 6 illustrates the side view of a bud during the course of opening.
FIG. 7 illustrates the side view of a flower during the course of opening with a few outer florets being fully expanded.
FIG. 8 illustrates an obverse view of a fully expanded flower.
FIG. 9 illustrates a reverse view of a fully expanded flower.
FIG. 10 illustrates a perspective view of a fully expanded flower.
FIG. 11 illustrates the top view of three typical outer ray-florets.
FIG. 12 illustrates the side view of three typical outer ray-florets.
FIG. 13 illustrates the top view of three typical inner ray-florets.

The chart used in the identification of colors described hereafter in the R.H.S. Colour Chart of The Royal Horticultural Society, London, England. In some instances more common color terms are provided and are to be accorded their usual dictionary significance. The plants described were grown at Nuaille, Trementines, France, in 20 cm. pots, three plants to a pot, and were rooted during early June and stopped during mid-July. All primary laterals were retained. Disbudding was carried out to leave the terminal flower heads, the plants were grown outdoors until late September, and then were grown in greenhouses provided at a minimum temperature of 15.5° C. These conditions are deemed to approximate those commonly utilized for the production of decorative pot mums.

Classification:

*Botanical.*—*Dendranthema grandiflora,* cv. 'Chanimba'.

*Commercial.*—Decorative pot mum.

Inflorescence

A. Capitulum:

*Form.*—Large, double, incurved, and commonly exhibiting a perfect configuration. The incurving commonly is particularly strong at the tips.

*Type.*—Pompon.

*Diameter across face.*—Approximately 10 to 12 cm. on average when fully expanded.

B. Corolla of ray and disk florets:

*Color of bud.*—Near Yellow Group 7B, merging to Yellow Group 7A towards the tip, and weakly tinged with red towards the base.

*Disk florets.*—Tubular, few in number, very difficult to observe, and tend to be scattered among the ray florets with a small cluster at the apex of the receptacle that is visible only when the ray florets are removed.

*General tonality.*—Bright yellow.

*Color of ray florets.*—When the flowers are fully expanded, the outer surfaces of most florets of the outer row are between Yellow Group 6C and Yellow Group 7C, and are very weakly tinged with red-purple towards the base. When the flowers are fully expanded, the inner surfaces of most florets of the outer row are Yellow Group 9B. When the outer row of florets is fully expanded, the inner surfaces of the inner florets are Yellow Group 9A.

*Configuration ray petals.*—The longitudinal axis of most petals is incurving with medium to strong degree of curvation at the tip. The longitudinal axis of the outer row of petals incurves strongly along most of the distal half. The cross-section of ray florets is concave. The length of the corolla tube is very short. The thickness of the ray florets is medium, and their surfaces are textured. The tips of the ray florets are pointed. The ray florets commonly are approximately 62 mm. in length and approximately 15 mm. in width on average.

C. Reproductive organs:

*Androecium.*—Generally present with the disc florets and absent in the ray florets.

*Gynoecium.*—Generally present with most disc florets and with most ray florets.

*Pollen.*—Formed in a sparse quantity, and golden-yellow in coloration.

*Fragrance.*—Typical of Chrysanthemum.

Plant

A. General appearance:

*Height.*—Very short to short, and approximately 30 to 35 cm. in height on average.

B. Foliage:

*Color.*—Between Green Group 137A and 147A.

*Configuration.*—Lobed (as illustrated).

*Texture.*—Fleshy.

*Serration.*—Medium to coarse.

*Length of lower lobe.*—Medium to long.

*Shape of base.*—Cordate.

*Claw in base of sinus between lateral lobes.*—Usually present.

*Margins of sinus between lateral lobes.*—Converging.

*Apex.*—Mucronate.

*Stems.*—Medium to strong, angular in cross section, somewhat brittle in nature, Yellow-Green Group 144A in coloration, and having anthocyanin coloration.

I claim:

1. A new and distinct cultivar of Chrysanthemum plant named 'Chanimba', substantially as herein shown and described, which (a) exhibits attractive large double incurved pompon blossoms that are bright yellow in coloration,
(b) exhibits a flower response period of approximately ten weeks,
(c) forms attractive dark green glossy foliage,
(d) achieves a very short to short plant height, and
(e) is particularly suited for pot mum production on a recurrent basis throughout the year.

* * * * *

CHAMMBA